United States Patent [19]

Landscheidt

[11] Patent Number: 4,605,740

[45] Date of Patent: Aug. 12, 1986

[54] PROCESS FOR THE PRODUCTION OF N-SUBSTITUTED ACRYLIC ACID AMIDES

[75] Inventor: Alfons Landscheidt, Krefeld, Fed. Rep. of Germany

[73] Assignee: Chemische Fabrik Stockhausen GmbH, Krefeld, Fed. Rep. of Germany

[21] Appl. No.: 534,535

[22] Filed: Sep. 22, 1983

[30] Foreign Application Priority Data

Sep. 24, 1982 [DE] Fed. Rep. of Germany ....... 3235398

[51] Int. Cl.⁴ .................. C07D 405/12; C07D 102/06; C07D 103/133; C07D 307/93
[52] U.S. Cl. .................................... 544/376; 544/226; 544/399; 544/151; 544/176; 549/463; 549/465; 549/467; 549/468; 564/135; 564/205; 546/196; 548/525; 548/540
[58] Field of Search ............... 544/151, 176, 226, 376, 544/399; 546/196; 548/525, 540; 549/463, 465, 467, 468; 564/135, 205

[56] References Cited

U.S. PATENT DOCUMENTS

| | | | |
|---|---|---|---|
| 2,719,175 | 9/1955 | Coover et al. | 260/561 |
| 2,719,178 | 9/1955 | Coover et al. | 260/562 |
| 3,813,438 | 5/1974 | Oshima et al. | 260/561 N |

OTHER PUBLICATIONS

Bartlett et al., C.A., vol. 97, 5547w, p. 5549, 1982.

*Primary Examiner*—Henry R. Jiles
*Assistant Examiner*—J. G. Mullins
*Attorney, Agent, or Firm*—Sprung Horn Kramer & Woods

[57] ABSTRACT

The present invention relates to a process for the production of N-substituted acrylic acid amides by conversion of 2-carboalkoxy-t-oxabicyclo(2,2,1)hept-5-enes with primary or secondary amines to 2-carboxamide-7-oxabicyclo(2,2,1)hept-5-enes and the thermal decomposition of the latter, preferably in the presence of Lewis acids and in a vacuum, to furane and N-substituted acrylic acid amides. The process according to the invention results in high purity N-substituted acrylic acid amides that are, in the main, free of bifunctional monomers which would disrupt the subsequent polymerization of the N-substituted acrylic acid amides by undesired cross-linking.

13 Claims, No Drawings

PROCESS FOR THE PRODUCTION OF N-SUBSTITUTED ACRYLIC ACID AMIDES

The present invention relates to a process for the production of N-substituted acrylic acid amides.

N-substituted acrylic acid amides are monomers with a double carbon bond, which are characterized by high polymerisation activity and as acid amides possess a hydrophilic and at the same time hydrolysis-stable functional group. For this reason, these monomers are of considerable technical interest.

For economic reasons, the lower esters of acrylic acids have been preferred for the production of other acrylic acid derivatives, including N-substituted amides. However, this is not performed by direct conversion of the acrylic acid ester with the amide. In place of the expected ester-amidation, there is firstly the addition of the amine to the activated carbon double bond in the sense of a Michael reaction, and then the second mole of the amine reacts with the ester to form the N-substituted 3-aminopropionic acid amide. This can be split pyrolitically to the corresponding N-substituted acrylic acid derivative (see U.S. Pat. No. 2,719,178).

The addition of an amine to the carbon double bond of an acrylic acid ester is thus greatly preferred over the ester-amidation. It is only at drastically higher temperatures that a reversal of reactivity occurs, since the Michaels reaction is then reversible. Because of this equilibrium, the amine can react irreversibly with the ester group (see U.S. Pat. No. 2,719,175).

If the required thermal loading and the associated impurity of the monomers is unacceptable, one is compelled to convert the carbon double bond of the acrylic acid ester with a protective group prior to the amidation of the ester. As in the situation described above, this can be brought about by the addition of an amine, although other proton-active materials, such as hydrogen halide, carbonic acid or alcohols can be added to the carbon double bond, and these double bond protecting groups removed after successful completion of the amidation under suitable reaction conditions.

A protective group of another kind is described in German Patent Application No. 22 17 623. Here, acrylic acid derivatives are converted to norbornene acid derivatives with cyclopentadiene in a Diels-Alder reaction. The N-substituted norbornene acid amide that is obtained by conversion of the amide in the second step is split into cyclopentadiene and the N-substituted acrylic acid amide by heating to 250° C. In this synthesis, also, the temperatures are too high for some especially sensitive monomers, to achieve the desired degree of purity.

The problem occurs particularly in the case of N-substituted acryl amides that contain a tertiary amino group. Monomers of this group are preferably converted to a high molecular weight, linear, water-soluble polymers. Proportions of only 10 ppm of bifunctional monomers can cause cross-linking which seriously detracts from the product quality of the water-soluble polymers. Thus, for example, N-allylacrylamide can result from N(N',N'-dimethylaminopropyl)acrylamide by thermal removal of dimethylamine; the formation of N-vinylacrylamide from N(N',N'-dialkylaminoethyl)acrylamide is analogously possible. The formation of these cross-linked monomers has to be supressed as far as possible in order to obtain monomers with sufficient purity to permit linear, gel-free, water-soluble polymers with molecular weights of over 10 million. This can only take place during the production of monomers that contain amino-groups by the application of controlled reaction conditions, i.e. lower temperatures.

Thus, it is an object of the present invention to provide a process for production of pure, N-substituted acrylic acid amides that are in the main free of unwanted bifunctional monomers that would subsequently lead to the formation of undesirable insoluble products upon polymerisation of the N-substituted acrylic acid amides.

Surprisingly, it has been found that 2-carboalkoxy-7-oxabicyclo(2,2,1)hept-5-enes, which are readily obtained by a Diels-Alder reaction of furane with acrylic acid esters, can be converted with primary or secondary amines by base catalysis to 2-carboxamide-7-oxabicyclo(2,2,1)hept-5-enes and which, after thermal removal of furane, will result in N-substituted acrylic acid amides of the required purity in accordance with the following:

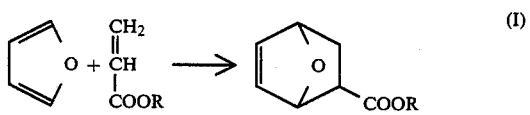

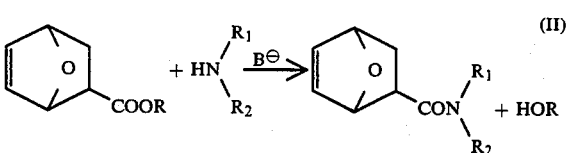

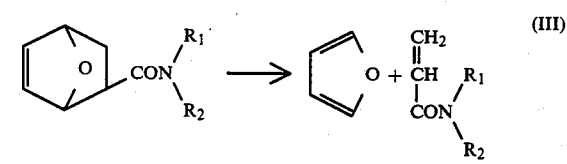

It was expected that 7-oxabicyclo(2,2,1)hept-5-ene would be transposed to benzol derivatives under the influence of bases. According to *Helvetica Chimica Acta*, Vol. 58 (1975), 1181, on treatment with potassium-t-butylate, a mixture of 10 parts O-tolunitrile and 1 part m-tolunitrile results from the Diels-Alder adduct of 2-methyl-furane and acrylnitrile.

The object of the present invention is realized by converting 2-carboalkoxy-7-oxabicyclo(2,2,1)hept-5-enes to 2-carboxamide-7-oxabicyclo(2,2,1)hept-5-enes with primary or secondary amines and decomposing same to yield furane and N-substituted acrylic acid amides.

The amidation of the 2-carboalkoxy-7-oxabicyclo(2,2,1)hept-5-enes is best done at temperatures that are below the decomposition temperature of the 7-oxabicyclo(2,2,1)hept-5-ene system. Temperatures between 20° C. and 60° C. are preferred. In order to achieve ester-amidation at these temperatures, water-free conditions and strong bases are generally required. Alkali metal alcoholates, hydrides, or amides—such as sodium methylate, sodium ethylate, sodium hydride, or potassium-t-butylate—are preferred as bases. Clearly, the use of basic ion exchangers or ester amidation under the conditions of phase-transfer catalysis are also possible.

After successful amidation, the catalyst is separated or neutralised and the resulting salt is separated by the addition of water. The N-substituted 2-carboxamide-7-oxabicyclo(2,2,1)hept-5-ene which results from the first stage of the reaction is then thermally decomposed to furane and N-substituted acrylic acid amide. This reaction is temperature dependent to a great extent. Even at room temperatures, partial decomposition will occur within a few weeks. Without the use of catalysts, however, it is necessary to heat to comparatively high temperatures between 60° and 300° C.—preferably between 80° and 200° C. and especially between 100° and 150° C. The addition of Lewis acids such as $AlCl_3$, $TiCl_3$, $SnCl_4$, $FeCl_3$, or $BF_3.OET_2$ will hasten the furane separation to a considerable extent at room temperature. Decomposition will then occur at room temperatures between 0° and 40° C.—preferably between 15° and 25° C. It is preferred that decomposition be performed by heating in a vacuum.

Primary or secondary amines can be used as the amines. Aliphatic, straight or branched chain primary or secondary amines as well as cyclic, aliphatic, heterocyclic or aromatic amines (if necessary, having additional functional groups) are suitable. Methylamine, ethylamine, propylamine, isopropylamine, butylamine, isobutylamine, 2-ethylhexylamine and stearylamine are examples of primary monoamines; dimethylamine and diethylamine are examples of secondary amines; ethylenediamine, 1,3-propylenediamine and 1,6-hexylenediamine are examples of primary diamines; morpholine, pyrrolidine and piperidine are examples of heterocyclic amines; and aniline, toluidine, anisidine, and N-methylaniline are examples of aromatic amines.

The process is particularly well suited for primary or secondary amines which contain at least one extra secondary or tertiary amino group, such as N,N-dimethylaminoethylamine, N,N-diethylaminoethylamine, N,N-dipropylaminoethylamine, N-ethylaminoethylamine, N-isopropylaminoethylamine, N-t-butylaminoethylamine, N,N-dimethylaminopropylamine, N,N,2,2-tetramethyl-1,3-diaminepropane, N,N-dimethylaminopropylamine, N,N-diethylaminopropylamine, N-methyl-piperazine, and N-methyl-N'(2-aminoethyl)-piperazine.

In most instances, the decomposition temperatures then lie below the boiling temperatures of the N-substituted acrylic acid amides under a technically-conventional vacuum, if the decomposition is performed without a Lewis acid catalyst. The greatest thermal loading of the synthesis product then occurs during the final distillation. The actual synthesis is carried out at lower temperatures. In particular, the occurrence of crosslinking with N-substituted acryl amides that contain an amino group is suppressed by this method. The purity of the additional monomers according to the process according to the present invention is also affected positively by the controlled reaction conditions.

The invention will now be described further by way of example only and with reference to the following:

EXAMPLE 1

2.4 parts 80% sodium hydride in paraffin oil are added to 88 parts N,N-dimethylaminoethylamine. 154 parts carbomethoxy-7-oxabicyclo(2,2,1)hept-5-ene are added drop-wise at 20° to 25° C. during cooling. The reaction medium is stirred for 15 hours and neutralised with 8 parts concentrated hydrochloric acid. 200 parts methylene chloride and 100 parts water are added, the organic phase separated, and the aqueous phase extracted four times with 50 parts methylene chloride in each instance. The combined organic phases are reduced in a rotary evaporator at a bath temperature of 90° C. and under a vacuum of 20 Torr. The residue is heated to 110° to 120° C. in a high vacuum (bath temperature 140° C.). After the conclusion of the furane separation, the sedimentation temperature increases and the product distills over. 106 parts N-(N'-N'-dimethylaminoethyl)-acrylamide with a boiling point of 100° C. at 8 Torr are obtained.

EXAMPLE 2

9 parts potassium-t-butylate are added to 121.8 parts N,N-diethylaminoethylamine. 154 parts 2-carboalkoxy-7-oxabicyclo(2,2,1)hept-5-ene are added drop-wise at 20° to 25° C. during cooling. The reaction medium is subsequently stirred for 15 hours and neutralised with 8 parts concentrated hydrochloric acid. 200 parts methylene chloride and 100 parts water are added, the organic phase separated off, and the aqueous phase extracted 4 times with 50 parts methylene chloride in each instance. The combined organic phases are reduced in a rotary evaporator at a bath temperature of 90° C. under a vacuum of 20 Torr. The residue is heated under vacuum at 110° to 120° C. (bath temperature 140° C.). After completion of the furane separation, the sedimentation temperature increases and the product distills over. 130 parts N-(N',N'-diethylaminoethyl)-acrylamide with a boiling point of 107° C. at 0.6 Torr are obtained.

EXAMPLE 3

53 parts 30% methanolic Na-methylate solution are added to 401.3 parts N,N-dimethylaminopropylamine. 577.5 parts 2-carbomethoxy-7-oxabicyclo(2,2,1)hept-5-ene are added drop-wise at 20° to 25° C. during cooling. The reaction medium is subsequently stirred for 15 hours and neutralised with 17.5 parts concentrated acetic acid. 1050 parts methylene chloride and 1050 parts water are added, the organic phase separated off and the aqueous phase extracted with 1050 parts methylene chloride. The combined organic phases are reduced in a rotary evaporator at a bath temperature of 90° C. and under a vacuum of 20 Torr. The residue is heated under a high vacuum to 110° to 120° (bath temperature 140° C.). At the conclusion of the furane separation, the sedimentation temperature increases and the product distills over. 368 g N-(N',N'-dimethylaminopropyl)-acrylamide with a boiling point of 100° C. at 0.3 Torr is obtained.

EXAMPLE 4

14.4 parts 30% methanolic Na-methylate solution are added to 130 parts N,N,2,2 tetramethyl-1,3-diaminopropane. 154 parts carbomethoxy-7-oxabicyclo(2,2,1)hept-5-ene are added drop-wise at 30° to 35° C. during cooling. The reaction medium is then stirred for 14 hours and neutralised with 7.85 parts 50% sulfuric acid. 200 parts methylene chloride and 100 parts water are added, the organic phase is separated off and the aqueous phase extracted 3 times with 50 parts methylene chloride in each instance. The combined organic phases are reduced in a rotary evaporator at 90° C. under a vacuum of 20 Torr. The residue is heated to 110° to 120° C. (bath temperature 140° C.) under a high vacuum. At the conclusion of the furane separation, the sedimentation temperature increases and the product distills over. 122.5 parts N-(N',N'2',2'-tetramethylaminopropyl)acrylamide with a boiling point of 110° at 0.6 Torr are obtained.

EXAMPLE 5

7.2 parts 30% methanolic Na-methylate solution are added to 29.5 parts n-propylamine. 84 parts 2-carboethoxy-7-oxabicyclo(2,2,1)hept-5-ene are added drop-wise at 30° C. during cooling. The reaction medium is then stirred for 15 hours, the crystalline mass is dissolved in 100 parts methylene chloride, and neutralised with 4 parts concentrated hydrochloric acid. 50 parts water are added, the organic phase is separated off, and the aqueous phase extracted 3 times with 25 parts methylene chloride in each instance. The combined organic phases are reduced in a rotary evaporator at a bath temperature of 90° C. and under a vacuum of 20 Torr. The residue is heated under a vacuum of 20 Torr to 110° to 120° C. (bath temperature 140° C.). At the conclusion of the furane separation, the sedimentation temperature increases and the product distills over at the now reduced pressure. 45 parts N-propylacrylamide of boiling point 88° C. at 0.8 Torr are obtained.

EXAMPLE 6

7.2 parts 30% methanolic Na-methylate solution and 77 parts 2-carbomethoxy-7-oxabicyclo(2,2,1)hept-5-ene are added to 134.8 parts stearylamine. The reaction medium is heated to 60° C. and stirred for 15 hours at this temperature. 300 parts of chloroform are next added and the mixture neutralised with 4 parts concentrated hydrochloric acid. 100 parts of water are added, the organic phase is separated off, and the aqueous phase extracted with 50 parts chloroform. The combined organic phases are reduced in a rotary evaporator at a bath temperature of 90° C. under a vacuum of 20 Torr. The residue is heated in a vacuum to 110° to 120° C. (bath temperature 140° C.). At the conclusion of the furane separation, the sedimentation temperature increases to 140° C. The mixture is cooled down, the product is dissolved in hot acetone, filtered, and allowed to recrystallise. 117 parts N-stearylacrylamide having a melting point of 75° to 77° C. are obtained.

EXAMPLE 7

7.2 parts 30% methanolic Na-methylate solution are added to 64.5 parts 2-ethylhexylamine. 77 parts 2-carbomethoxy-7-oxabicyclo(2,2,1)hept-5-ene are added drop-wise at 30° to 35° C. during cooling. The reaction medium is then stirred for 15 hours and neutralised with 4 parts concentrated hydrochloric acid. 100 parts methylene chloride and 50 parts water are added, the organic phase separated off, and the aqueous phase extracted twice with 25 ml methylene chloride in each instance. The combined organic phases are reduced in a rotary evaporator at a bath temperature of 90° C. and a vacuum of 20 Torr. The residue is heated under a high vacuum to 110° to 120° C. (bath temperature 140° C.). On conclusion of the furane separation, the sedimentation temperature increases and the product distills over. 66.6 parts N(2-ethylhexyl)acrylamide with a boiling point of 123° C. at 0.4 Torr are obtained.

EXAMPLE 8

7.2 parts 30% methanolic Na-methylate solution are added to 43.5 parts morpholine. 77 parts 2-carbomethoxy-7-oxabicyclo(2,2,1)hept-5-ene are added drop-wise at 30° to 35° C. during cooling. The reaction medium is then stirred for 15 hours and neutralised with 4 parts concentrated hydrochloric acid. 100 parts methylene chloride and 50 parts water are added, the organic phase separated off, and the aqueous phase extracted 4 times with 25 parts methylene chloride in each instance. The combined organic phases are reduced in a rotary evaporator at a bath temperature of 90° C. and under a vacuum of 20 Torr. The residue is heated under a vacuum of 20 Torr to 110° to 120° C. (bath temperature 140° C.). On conclusion of the furane separation, the sedimentation temperature increases and the product distills over at the now-reduced pressure. 48 parts N-morpholinoacrylamide with a boiling point of 87° C. at 1 Torr are obtained.

EXAMPLE 9

7.2 parts 30% methanolic Na-methylate solution are added to 36.5 parts diethylamine. 77 parts 2-carbomethoxy-7-oxabicyclo(2,2,1)hept-5-ene are added drop-wise at 40° C. The reaction medium is then stirred for 15 hours at this temperature and neutralised with 4 parts concentrated hydrochloric acid. 100 parts methylene chloride and 50 parts water are added, the organic phase separated off, and the aqueous phase extracted 3 times with 25 parts methylene chloride in each instance. The combined organic phases are reduced in a rotary evaporator at a bath temperature of 90° C. and under a vacuum of 20 Torr. The residue is heated under a vacuum of 20 Torr to 110° to 120° C. (bath temperature 140° C.). On conclusion of the furane separation, the sedimentation temperature increases and the product distills over at the now lowered pressure. 21 parts N,N-diethylacrylamide with a boiling point of 55° C. at 1 Torr are obtained.

EXAMPLE 10

7.2 parts 30% methanolic Na-methylate solution are added to 15 parts ethylenediamine. 77 parts 2-carbomethoxy-7-oxabicyclo(2,2,1)hept-5-ene are added drop-wise at 30° C. during cooling. Recrystallisation is then allowed to proceed overnight and the crystalline mass is dissolved in 400 parts chloroform, and neutralised with 4 parts concentrated hydrochloric acid. 50 parts water are added, the organic phase separated off, and the aqueous phase extracted 5 times with 50 parts chloroform in each instance. The combined organic phases are reduced in a rotary evaporator at a bath temperature of 90° C. and under a vacuum of 20 Torr. The residue is heated in a vacuum of 10 Torr to 110° to 120° C. (bath temperature 140° C.). On conclusion of the furane separation the sedimentation temperature increases to 140° C. After cooling, the product is dissolved in hot n-butanol, filtered, and allowed to recrystallise at 0° C. 27 g N,N'-ethylenebisacrylamide with a melting point of 150° to 155° C. is obtained.

EXAMPLE 11

7.2 parts 30% methanolic Na-methylate solution are added to 46.5 parts aniline. 77 parts 2-carbomethoxy-7-oxabicyclo(2,2,1)hept-5-ene are added drop-wise at 40° C. The reaction medium is then stirred for 15 hours at this temperature and neutralised with 4 parts concentrated hydrochloric acid. 50 parts water are added, and the organic phase separated off. The organic phase is reduced in a rotary evaporator at a bath temperature of 90° C. and under a vacuum of 20 Torr. The residue is heated in a vacuum of 20 Torr to 110° to 120° C. (bath temperature 140° C.). On conclusion of the furane separation, the sedimentation temperature increases and the product distills over. 27.5 parts N-phenylacrylamide with a boiling point of 135° C. at 0.4 Torr are obtained.

The product recrystallised from the acetonitrile at −20° C. has a melting point of 114° to 115° C.

EXAMPLE 12

7.2 parts 30% methanolic Na-methylate solution are added to 29.5 parts n-propylamine. 84 parts 2-carboethoxy-7-oxabicyclo(2,2,1)hept-5-ene are added dropwise at 30° C. The reaction medium is then stirred for 15 hours and the precipitated crystalline mass dissolved in 100 parts methylene chloride and neutralised with 4 parts concentrated hydrochloric acid. 50 parts water are added, and the organic phase separated off. The aqueous phase is extracted 3 times with 25 parts methylene chloride in each instance. The combined organic phases are dried with magnesium sulfate and reduced in a rotary evaporator at a bath temperature of 40° C. and under a vacuum of 20 Torr. After the addition of 2.2 parts $AlCl_3$, the resulting furane is distilled off under the same conditions and 100 parts methylene chloride and 50 parts water are added to the residue. The organic phase is separated off and the aqueous phase extracted 3 times with 25 parts methylene chloride in each instance. The combined organic phases are reduced in a rotary evaporator and the residue is distilled in a vacuum. 45 parts N-propylacrylamide with a boiling point of 88° C. at 0.8 Torr are obtained.

The embodiments of the invention in which an exclusive property or privilege is claimed are defined as follows:

1. A process for the production of N-substituted acrylic acid amides, which comprises converting a 2-carboalkoxy-t-oxabicyclo(2,2,1)hept-5-ene to a 2-carboxamide-7-oxabicyclo(2,2,1)hept-5-ene with a primary or secondary amine selected from the group consisting of N,N-dimethylaminoethylamine, N,N-diethylaminoethylamine, N,N-dipropylaminoethylamine, N-ethylaminoethylamine, N-isopropylaminoethylamine, N-t-butylaminoethylamine, N,N-dimethylaminopropylamine, N,N,2,2-tetramethyl-1,3-diaminepropane, N,N-diethylaminopropylamine, N-methyl-piperazine and N-methyl-N'(2-aminoethyl)-piperazine, and thermally decomposing said 2-carboxamide-7-oxabicyclo(2,2,1)hept-5-ene to furane and the N-substituted acrylic acid amide.

2. A process according to claim 1, wherein the conversion of said 2-carboalkoxy-t-oxabicyclo(2,2,1)hept-5-ene with said primary or secondary amine is carried out at a temperature between 20° and 60° C.

3. A process according to claim 1, wherein the conversion of said 2-carboalkoxy-7-oxabicyclo(2,2,1)hept-5-ene with said primary or secondary amine is carried out under water-free conditions and in the presence of a strong base or basic ion exchanger.

4. A process according to claim 3, wherein said strong base is selected from alkali metal alcoholates, anhydrides and amides.

5. A process according to claim 1, characterized in that the 2-carboxamide-7-oxabicyclo(2,2,1)hept-5-ene is decomposed to furane and N-substituted acrylic acid amides by heating to a temperature between 60° and 300° C.

6. A process according to claim 5, wherein said temperature is between 80° and 200° C.

7. A process according to claim 5, wherein said temperature is between 100° and 150° C.

8. A process according to claim 1 wherein the decomposition of the 2-carboxamide-7-oxabicyclo(2,2,1)hept-5-ene is carried out in the presence of Lewis acids at a temperature between 0° and 40° C.

9. A process according to claim 8, wherein said temperature is between 15° and 25° C.

10. A process according to claim 8, wherein said Lewis acid is selected from $AlCl_3$, $TiCl_4$, $SnCl_4$, $FeCl_3$ and $Bf_3OET_2$.

11. A process according to claim 1 wherein the decomposition of the 2-carboxamide-7-oxabicyclo(2,2,1)hept-5-ene is carried out by heating in a vacuum.

12. A process according to claim 1, wherein said amine is a straight or branched-chain aliphatic or cycloaliphatic amine.

13. A process according to claim 1, wherein said amine is N-methyl-piperazine or N-methyl-N'(2-aminoethyl)-piperazine.

* * * * *